(12) United States Patent
Berestov (10) Patent No.: US 6,829,383 B1
(45) Date of Patent: Dec. 7, 2004

(54) STOCHASTIC ADJUSTMENT OF DIFFERENTLY-ILLUMINATED IMAGES

(75) Inventor: Alexander Berestov, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/561,291

(22) Filed: Apr. 28, 2000

(51) Int. Cl.[7] .............................. G06K 9/00; G06K 9/40; A61B 3/14; A61B 3/00
(52) U.S. Cl. ...................... 382/154; 382/294; 382/274; 396/18; 348/78; 351/200; 359/462; 345/419
(58) Field of Search .................... 382/116–118, 274, 382/154, 218–220, 294, 309; 348/78, 578; 396/18; 340/5.52, 5.82; 356/12, 71; 902/3, 6; 713/186; 351/200, 201, 206, 221, 240; 359/462, 464–472; 345/419–427

(56) References Cited

U.S. PATENT DOCUMENTS

| | | | | |
|---|---|---|---|---|
| 5,187,754 A | * | 2/1993 | Currin et al. | 382/284 |
| 5,537,638 A | * | 7/1996 | Morita et al. | 345/426 |
| 6,075,905 A | * | 6/2000 | Herman, et al. | 382/284 |
| 6,454,410 B1 | * | 9/2002 | Berger et al. | 351/206 |
| 6,459,821 B1 | * | 10/2002 | Cullen | 382/294 |
| 6,520,640 B1 | * | 2/2003 | Binnun | 351/206 |

OTHER PUBLICATIONS

Yogesan, K., Eikelboom, R., and Barry, C. Colour Matching of Serial Retinal Images. Lions Eye Institute and Centre for Ophthalmology and Visual Science [online], Feb. 1999 [retrieved on Jun. 27, 2000]. Retrieved from the Internet:<URL: http://www.general.uwa.edu.au/u/robeik/OSA99/>.

Woods, A. et al;. *Image Distortions in Stereoscopic Video Systems*, SPIE vol. 1915 Stereoscopic Displays and Applications, pp 36–48, IV (1993).

* cited by examiner

Primary Examiner—Jayanti K. Patel
Assistant Examiner—Aaron Carter
(74) Attorney, Agent, or Firm—Fitzpatrick, Cella, Harper & Scinto

(57) ABSTRACT

A computer-implemented method and system for equalizing the brightness, contrast and color of two or more images (206, 208) of an eye fundus (106). Because left and right images (206, 208) are taken from different camera (104) positions, or because two images (206, 208) have been taken at different times, the resulting images (206, 208) have different brightness, contrast and color. Groups (306, 308) are formed from the pixels making up the images (206, 208). The groups can be straight lines oriented perpendicularly to the direction of camera (104) motion. The intensity of each pixel in a group is measured, and the group's mean and variance are then calculated. The intensity of the groups are then adjusted in order that a group (306) from the left image (206) will have the same mean intensity and variance as the corresponding group (308) from the right image (208). The measurements and adjustments can be made for each of the red, green and blue intensities of each pixel.

15 Claims, 8 Drawing Sheets (5 of 8 Drawing Sheet(s) Filed in Color)

STOCHASTIC ADJUSTMENT OF DIFFERENTLY-ILLUMINATED IMAGES

CROSS REFERENCE TO RELATED APPLICATIONS

The subject matter of this application is related to the subject matter of the following applications: Ser. No. 09/428,286, entitled "Fast Epipolar Line Adjustment of Stereo Pairs," by Alexander Berestov and filed on Oct. 27, 1999; and Ser. No. 09/500,181, entitled "Detection and Removal of Image Occlusion Errors," by Alexander Berestov and filed on Feb. 7, 2000. Each of these applications is assigned to the assignee of the present invention. The above applications are incorporated by reference herein in their entirety.

BACKGROUND OF THE INVENTION

1. Field of the Invention

The present invention relates generally to the field of image processing, and more particularly, to the stochastic adjustment of fundus images having different brightness, contrast and color.

2. Description of Background Art

Figure 1:
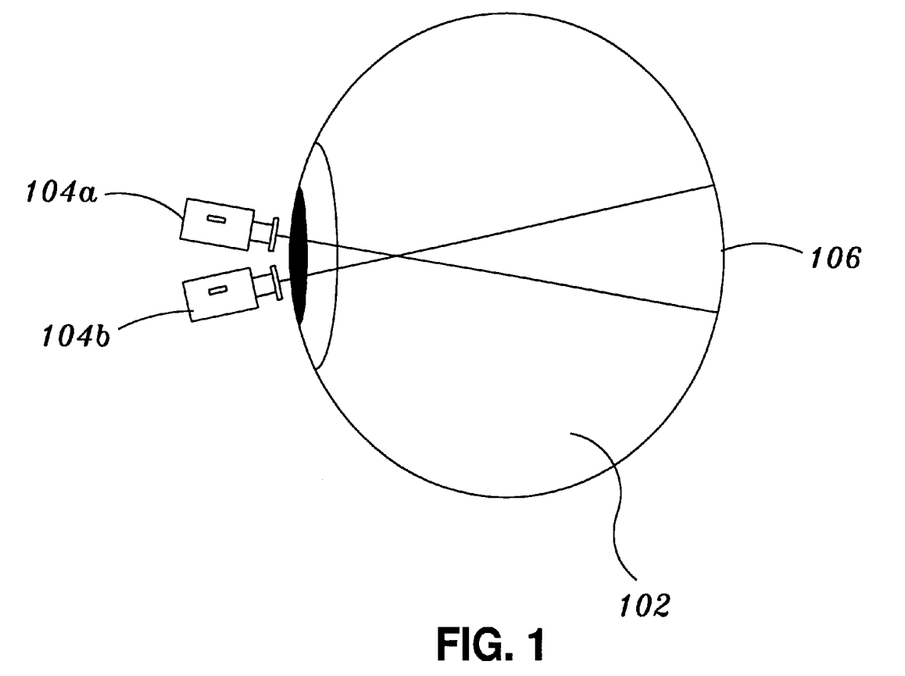
FIG. 1 is a diagram illustrating the illumination of a fundus from two different camera positions.
Figure 2A:
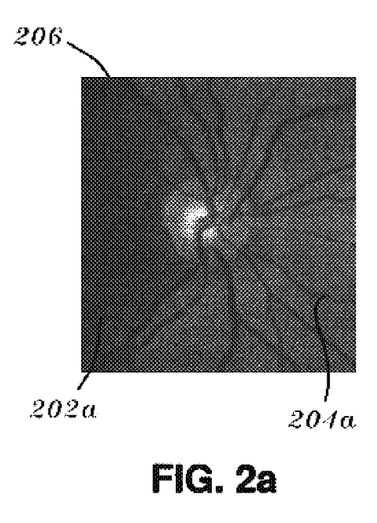
FIGS. 2a and 2b are left and right images, respectively, of an ocular nerve.
Figure 2B:
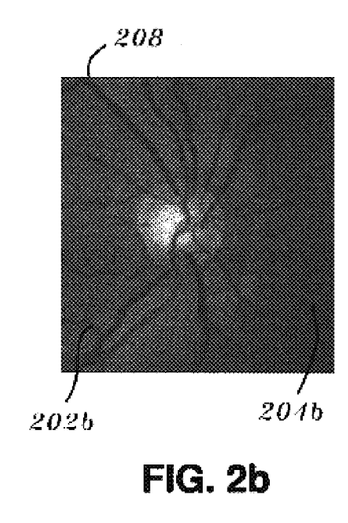

It is often necessary to view images of an object such as an eye fundus in stereo in order to analyze the three-dimensional structure of the object, the distance from the image capture device to the object, or to measure spatial changes over time. Usually, stereo photographs of the human eye fundus are taken with one camera shifted by a small distance, illuminating the fundus through the pupil as illustrated in FIG. 1. The shape of the eye fundus is generally spherical, so the difference in color and brightness between stereo images depends on the position of the camera, which illuminates the fundus through the pupil at different angles. For example, FIGS. 2a and 2b show a left and right image of an ocular nerve. In the figure, the left part of the left image in FIG. 2a is darker than the left part of the right image in FIG. 2b, and the right part of the right image is darker than the right part of the left image. In order to be able to perform a matching analysis on the images and create a topographical representation of the fundus, these illumination errors must be substantially reduced or eliminated. In addition, it is often desirable to compare two images of the same fundus taken at different times, or with different cameras. This additionally presents a situation where the illumination in each image may be different, requiring correction before appropriate analysis can take place.

It is possible to adjust the brightness, contrast and color of two images using a histogram adjustment method, as proposed by Kanagasingam Yogesan, Robert H. Eikelboom and Chris J. Barry in their paper, "Colour Matching of Serial Retinal Images," Lions Eye Institute and Centre for Ophthalmology and Visual Science, Perth, Western Australia, Australia, which is incorporated by reference herein in its entirety. In their paper, the authors propose a color-matching algorithm that equalizes the mean and standard deviation of each of the three colors in the image. First, the entire image is split into the colors red, green and blue; the mean and standard deviation are calculated, and then the histograms of both images are adjusted to equalize the images. The color image is reconstituted by recombining the three channels. The problem with this method of adjustment is that the equalization adjustment is made for the whole image, so the differences in illumination within the images remain unchanged. For example, consider the points 202a and 202b in FIGS. 2a and 2b, respectively. From the figures, it can be seen that point 202a is much darker than point 202b. However, since 202a and 202b actually are the same point on the eye fundus, both points should ideally be illuminated equivalently. Because the Kanagasingram et al. method uses a histogram to adjust the brightness of the whole image, if FIG. 2a were lightened, for example, points 202a and 202b might end up being equally bright, but point 204a, which was originally lighter than point 204b, would now be even brighter, causing increased differences in illumination between the points 204a and 204b. Thus, adjusting the entire image to compensate for different illumination is not a satisfactory solution.

Therefore, what is needed is a way of adjusting differently illuminated images of an eye fundus to compensate for different lighting conditions.

DISCLOSURE OF INVENTION

In accordance with the present invention, there is provided a system and method for adjusting differently illuminated images of an eye fundus (106) to reduce and eliminate illumination errors. In one embodiment, two or more images (206, 208) are obtained by an image receiving device (502) that is coupled to a processing computer (500). In another embodiment, the images exist on film or paper, and are converted into computer-readable form by a scanning device. Pixels within each image are assigned to groups (306, 308) of a selected width. Each group forms a line through the image. The lines may be either straight or curved, although a selection of longitudinally-curved lines allows for greater reduction in illumination errors. Each group (306) in the first image (302) is associated with a corresponding group (308) in the other images. Next, the intensity level for at least one color channel is determined for each pixel in each group (306, 308). From this data, the mean intensity level for each group (306,308) is then determined. In one embodiment, the variance of each group (306, 308) is additionally determined. The mean intensity levels for each group (306, 308) are compared in each image (302, 304), and the intensity level of pixels in one or more images are then adjusted so that the $n^{th}$ group in each image will have approximately equal mean intensity levels.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other more detailed and specific objects and features of the present invention are more fully disclosed in the following specification, reference being had to the accompanying drawings, in which.

DETAILED DESCRIPTION OF THE PREFERRED EMBODIMENTS

Referring now to FIG. 1, there is shown an eye 102, including a fundus 106, and a camera 104, the camera 104 being shown in two different positions 104a and 104b. For illustrative purposes, the camera 104 is show as being in both locations 104a and 104b simultaneously. As can be seen from the figure, a light source attached to the camera and projecting a narrow beam of light that can penetrate through the pupil will not uniformly illuminate the eye 102, or portions thereof, e.g., the fundus 106, because of the narrowness of the beam of light. This non-uniform illumination results in the disparity in contrast and intensity described above.

Referring now to FIGS. 2a and 2b, there are shown two images of the eye fundus. FIG. 2a is a left image and FIG. 2b is a right image. The images are photographs taken by a camera 104 designed for fundus imaging. One such camera is the TRC-NW5S by TOPCON American Corporation of Paramus, N.J. Those skilled in the art will appreciate that other cameras and imaging devices could be substituted for the TRC-NW5S, and may include, for example, film cameras, digital cameras, and video cameras. The images that are to be captured are, in a preferred embodiment, visible spectrum images; however, infrared images and images displaying other spectrums may be used in alternative embodiments.

Figure 3A:
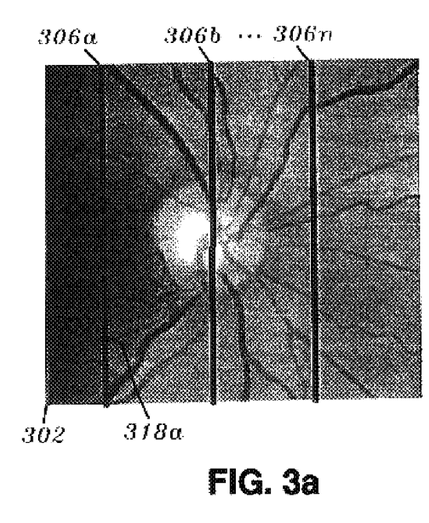
FIGS. 3a and 3b are left and right images, respectively, of an ocular nerve with superimposed lines of pixels.
Figure 3B:
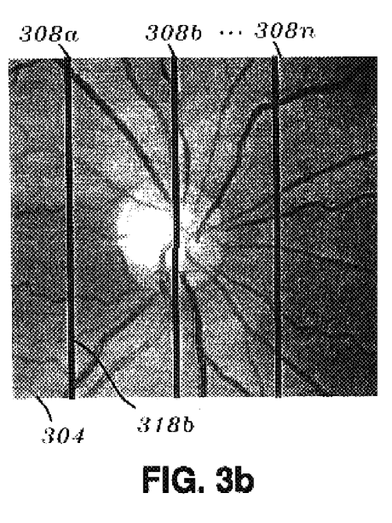

Referring now to FIGS. 3a and 3b, after the two images 206, 208 are captured, pixels within the images 206, 208 are separated into groups 306a, 306b, ... 306n in the left image 302, and groups 308a, 308b, ... 308n in the right image 304. In one preferred embodiment, pixels may be grouped so as to form a straight line, as illustrated in FIGS. 3a and 3b, while in another preferred embodiment, they may be grouped to form longitudinal lines. In yet other embodiments, pixels may be grouped in lines of other curvatures, but as those skilled in the art will recognize, because of the curved shape of the fundus 106, longitudinal lines will tend to result in more accurate elimination of illumination errors. One embodiment has the pixels grouped in straight lines perpendicular to the direction of movement of the camera 104. An alternative embodiment has the pixels grouped in longitudinal lines, with the lines perpendicular to the direction of movement at their point of intersection with the direction of movement. In still other embodiments, the pixels may be grouped into either straight or longitudinal lines that are not perpendicular as described above, although such a grouping may consequently result in removing fewer illumination errors. The pixels in a group 306 may be as narrow as one pixel, or as wide as the entire image. Those skilled in the art will recognize that narrower groups allow for greater accuracy in detecting illumination errors.

Figure 5:
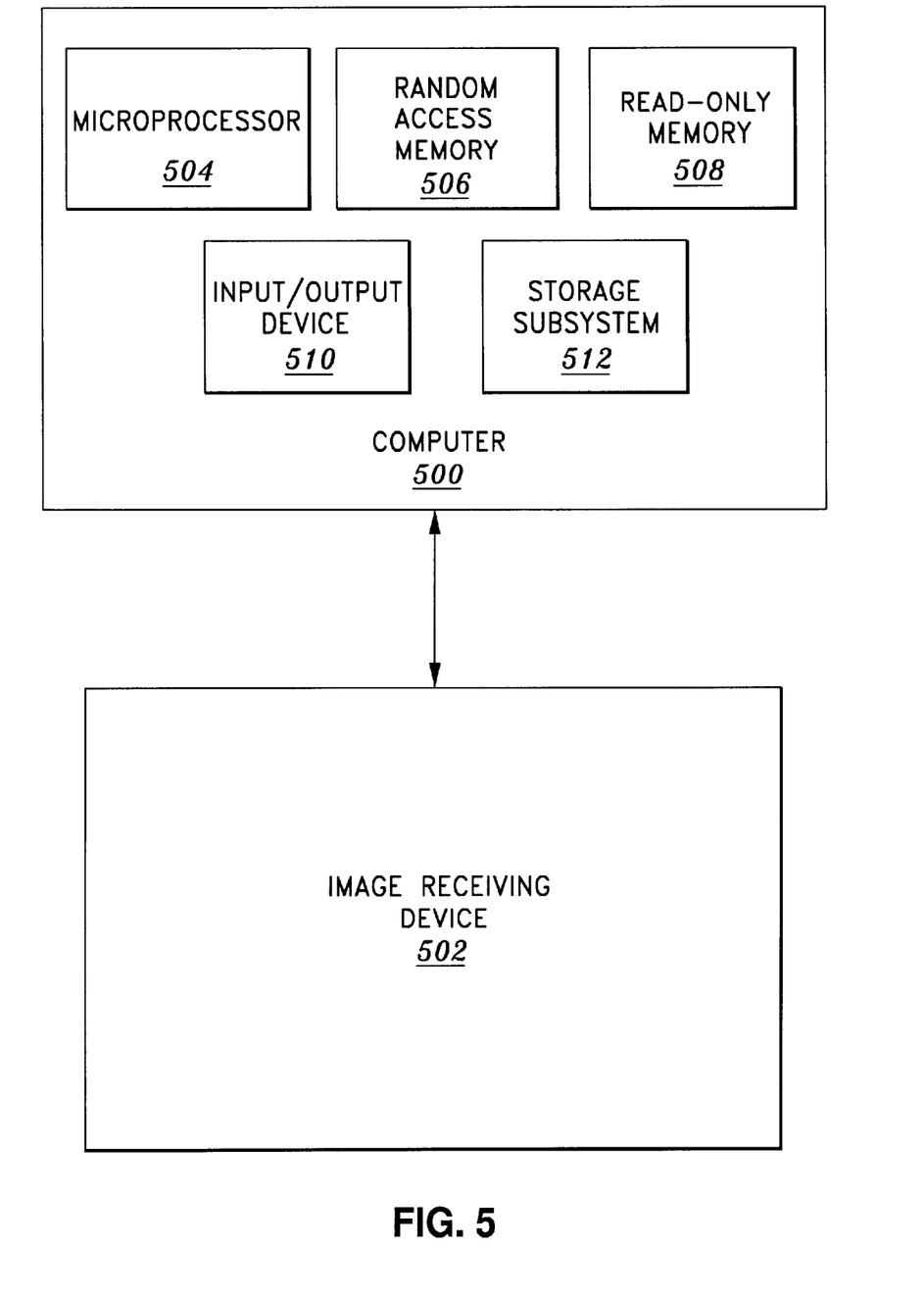
FIG. 5 is a block diagram of a computer system for processing captured images.

In a preferred embodiment, the image processing is performed by a computing device 500, which is attached to the image receiving device 502, as illustrated in FIG. 5. The computing device 500 receives input from the image receiving device 502 via an input/output device 510. The computing device is controlled by a microprocessor 504, which may be a conventional microprocessor such as the Pentium® III by Intel Corporation, Santa Clara, Calif. The computing device 500 additionally may contain conventional random access memory (RAM) 506 for storing instructions and for providing fast access to relevant data, and conventional read-only memory (ROM) 508 for storing program code and other required data. A storage subsystem 512 may also be present for storing data and images received from the image receiving device 502, and for subsequent processing of those images. The image receiving device 502 may be attached directly to the computing device 500, as in the case of digital or video imaging devices. In other embodiments, however, the image receiving device 502 may be a film camera, and the film may be processed in a conventional manner, and the resulting film images supplied to the computing device 500, e.g. via a conventional scanner (not shown). The storage subsystem 512 may be either internal to the computing device 500, or else may be located externally.

The groups to be selected are identified by the processor 504, which then performs calculations based upon the data stored in RAM 506, ROM 508, or in the storage subsystem 512, that correspond to the identified pixels in the groups.

In a preferred embodiment, and as assumed for purposes of this description, the eye 102 remains substantially motionless between capture of the left and right images, and the camera or imaging devices 104 travels in a horizontal direction. In alternative embodiments, however, the camera 104 can move in a vertical or diagonal direction. In yet other alternative embodiments, the camera 104 can remain in a fixed position, and the eye 102 may move or rotate.

After selecting the pixel groups 306, 308, pixels in each group are measured by the computing device 500 to determine their intensity. In a preferred embodiment, the red, green and blue intensity levels for each pixel are each measured. In an alternative embodiment, other color channels may be used, for example cyan, yellow and magenta. In still other embodiments, intensity values may be calculated for each pixel as a function of grayscale values of color components.

Each pixel along a given line has an associated intensity. In a preferred embodiment, the intensity of each of the red, green and blue color components that are present in each pixel in a group is calculated, and the mean intensity value of each group and its variance are calculated for each of the three colors. Then each pixel in a group of the left image 302 is compared to the corresponding pixel in the same group of the right image 304.

Because either the camera 104 or the eye 102 or both have moved between images, the left-most pixels of the left image 302 may not represent the same part of the fundus 106 as the left-most pixels of the right image 304. Thus, any information that is already known, for example the distance the camera 104 has moved between images, can be used to improve accuracy. In addition, a conventional matching algorithm known by those skilled in the art and described, for example, in G. Xu and Z. Zhang, *Epipolar Geometry in Stereo, Motion and Object Recognition*, Kluwer Academic Publishers, Dordrecht, 1996, pp. 221–245, which is incorporated by reference herein in its entirety, may be employed to identify corresponding pixels in each image 302, 304. In another embodiment, however, it may be assumed that the location of a group in the left image 302 will be the same as the location of the corresponding group in the right image 304.

The intensity of each individual pixel is then recalculated in either or both images to yield associated pixels of approximately equal intensity. For example, point 318a is a pixel in the left image 302, and point 318b is the corresponding pixel in the right image 304. After the images are arranged into groups, point 318a will be part of group 306a, and point 318b will be part of corresponding group 308a. As can be seen from the left 302 and right 304 images, the left point 318a is considerably darker in than the corresponding right image point 318b. Next, the mean intensity values and the variances for groups 306a and 308a are calculated.

For example, if $X_1$ and $X_2$ are discrete random variables with values $\{x^1_i\}$ and $\{x^2_i\}$, then the expected or mean values of $X_{1,2}$ are defined by $$EX_{1,2} = \mu_{1,2} = \sum_i x_i^{1,2} p(x_i^{1,2}), \quad (1)$$

where p is the probability function. The quantities $$EX^2_{1,2} - \mu^2_{1,2} = \sigma^2_{1,2} \quad (2)$$

are the variances of $X_{1,2}$ or the expected values of the square of the deviations of $X_{1,2}$ from their expected values. Variables $X_{1,2}$ should be adjusted so that the expected values $\mu_{1,2}$ and variances $\sigma^2_{1,2}$ are the same for both variables. In the simplest case, a linear transformation may be used:

$$X_2 = aX_1 + b, \quad (3)$$

where a and b are constant parameters. Substitution of (3) into (1) and (2) gives:

$$b = \mu_2 - a\mu_1, \quad (4)$$
$$a = \sqrt{\frac{\sigma_2^2}{\sigma_1^2}}.$$

Assume the pixel brightness level in the pixel of point 318a is $X_1$ and in the pixel of point 318b is $X_2$. This provides the mechanism of image adjustment. Expected values and variances for both groups 306a and 308a can be calculated using a probability function such as p=1/H, where H is the number of pixels along the lines in the image. Those skilled in the art will appreciate that other probability functions could be used, such as exponential, normal, or functions derived from the data. In addition, higher order moments could also be used for more accurate adjustments.

The next step is to recalculate pixel brightness in one or both images using equation (3), for example. One image may be adjusted to the other, or both images may be adjusted to some values $\mu$ and $\sigma^2$. For example, average values such as $\mu = (\mu_1 + \mu_2)/2$, exponential values $\sigma^2 = (\sigma^2_1 + \sigma^2_2)/2$, or some other desirable values could be used.

This adjustment is made for every separated color component, and the results may then be recombined in order to obtain adjusted color images. It is also possible to estimate the average disparity and to equalize the expected value and variance in the shifted groups, in order to obtain a more precise result.

Figure 4A:
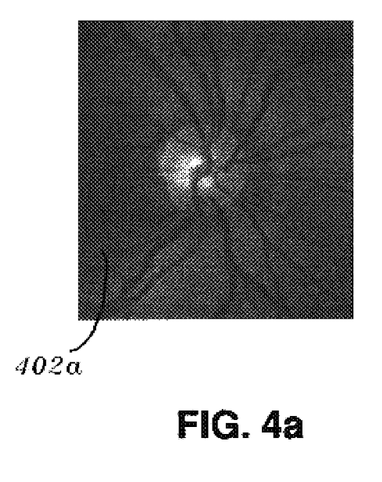
FIGS. 4a and 4b are illumination-corrected left and right images, respectively, of an ocular nerve.
Figure 4B:
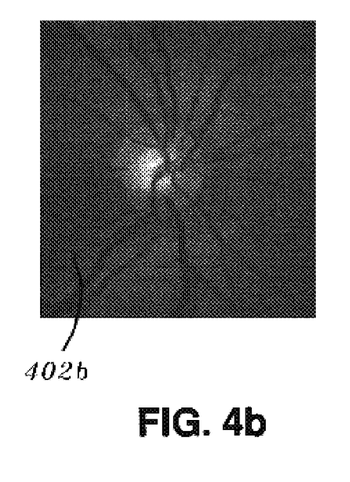

FIGS. 4a and 4b depict the results of the adjustment where p=1/H, $\mu = (\mu_1 + \mu_2)/2$, $\sigma^2 = (\sigma^2_1 + \sigma^2_2)/2$. FIG. 4a is the left image (corresponding to FIG. 2a) after the adjustment, and FIG. 4b is the right image (corresponding to FIG. 2b) after the adjustment. As can be seen, whereas points 202a and 202b had different intensity levels, the same points 402a and 402b do not noticeably differ in their intensity after the adjustment.

Figure 7A:
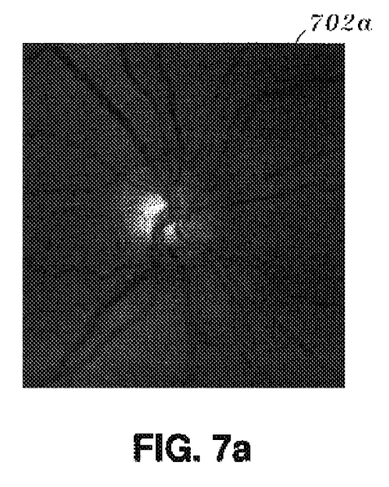
FIG. 7a is an anaglyph of an uncorrected image pair of an ocular nerve.
Figure 7B:
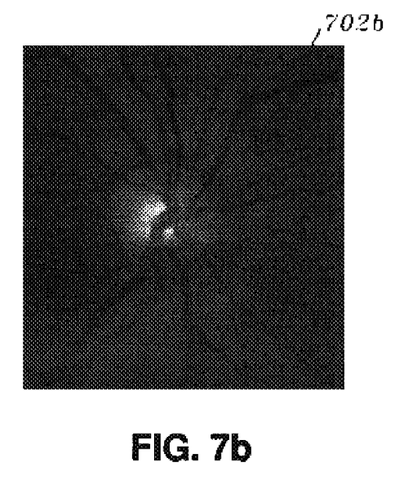
FIG. 7b is an anaglyph of an illumination-corrected image pair of an ocular nerve.

The results may also be seen by reference to FIGS. 7a and 7b. FIG. 7a is an anaglyph image of a fundus 106. The differences resulting from illumination errors are visible as a red tint toward the right hand side of the image, including point 702a. FIG. 7b is an anaglyph of the same fundus 106 after the adjustment has been made. Even without the use of colored filters to view the anaglyph, it can be seen that the red tint at point 702a is not present at the corresponding point 702b in the adjusted image of FIG. 7b, indicating that the illumination errors have been significantly reduced or eliminated.

Figure 8A:
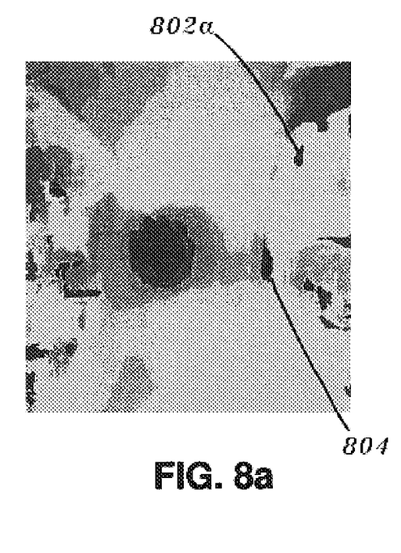
FIG. 8a is a disparity map of an uncorrected image pair of an ocular nerve.
Figure 8B:
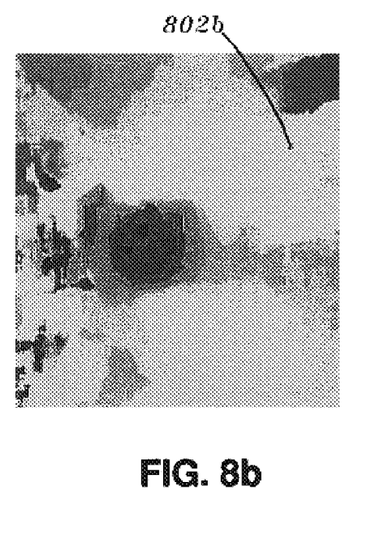
FIG. 8b is a disparity map of an illumination-corrected image pair of an ocular nerve.

FIG. 8a is a disparity map of the images of FIG. 2, and FIG. 8b is a disparity map of the images of FIG. 4. In both FIGS. 8a and 8b, illumination errors are represented by abrupt changes in color, as at points 802a, 802b, and 804. Note that errors in the left parts of FIGS. 8a and 8b are related to camera distortions, or caused by other phenomenon such as vertical parallax, and must be corrected by other means, such as epipolar adjustment. After the adjustment has been made, the error at point 802a has been significantly reduced to point 802b, and the error at point 804 has been eliminated. As may be seen from the figures, other errors present in FIG. 8a have also been eliminated in FIG. 8b.

Figure 6:
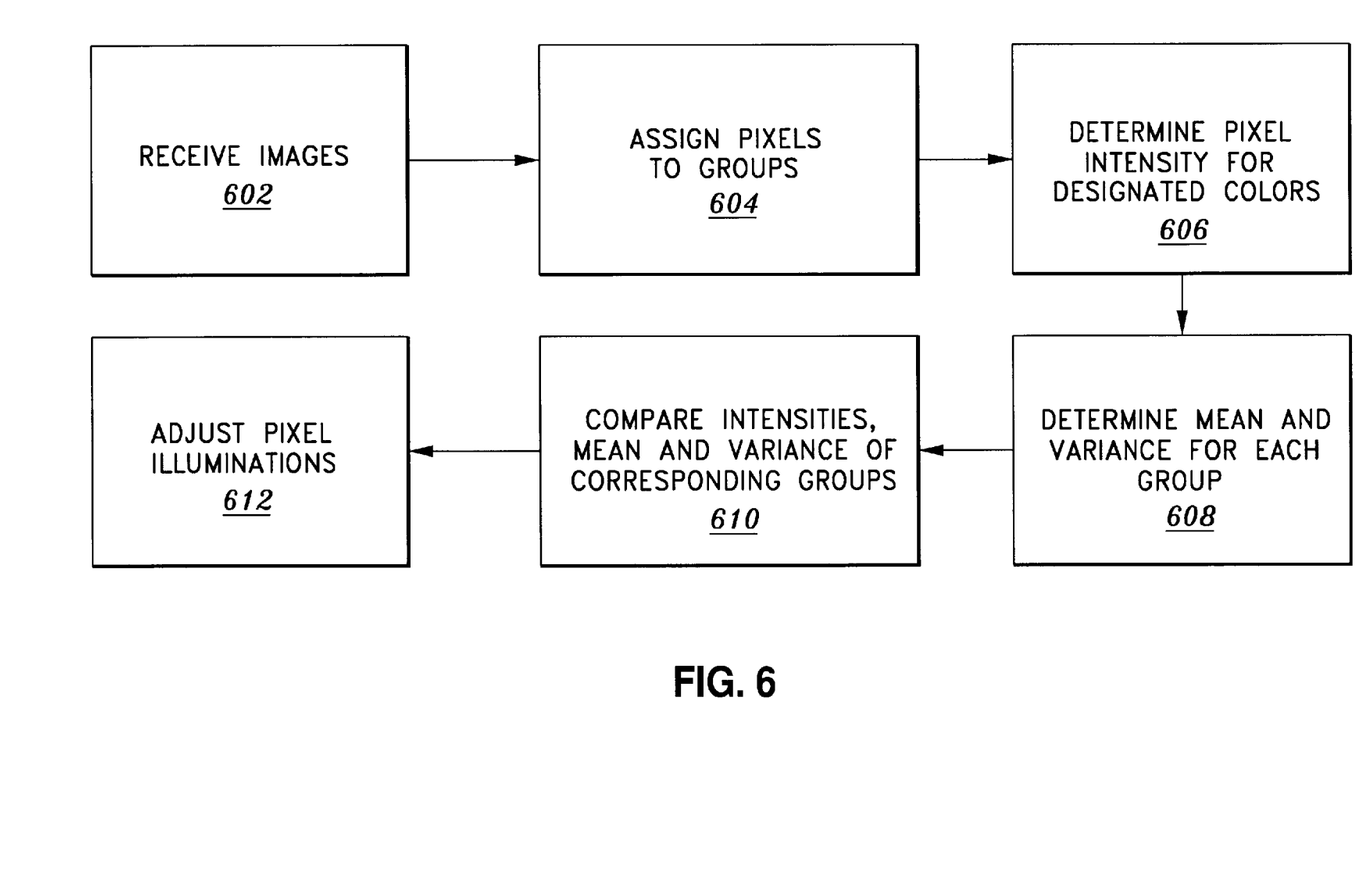
FIG. 6 is a flow chart illustrating the operation of an embodiment of the present invention.

Referring now to FIG. 6, there is shown a flow chart of the operation of one embodiment of the present invention. The computing device 500 receives 602 the images to be processed. The pixels are then grouped 604, e.g., into straight or longitudinal lines, and the pixel intensities for the designated groups are then determined 606. Next, a mean and variance for each group is determined 608, and the intensities, mean and variance of corresponding groups are compared 610. Finally, the pixel intensities are adjusted 612, resulting in the elimination of illumination errors between the two images. Additional details regarding each of these steps are described above. It will be understood by those skilled in the art that the order of steps described by FIG. 6 is merely one preferred embodiment of the present invention, and that the various steps may be performed in alternative steps. For example, the step of determining which groups correspond to each other in each image may be performed immediately after the groups are determined. In yet another embodiment, the intensities of the pixels may be adjusted only for one color instead of three. Still other changes to the execution order of the steps of the present invention will be readily apparent to those skilled in the art.

While the invention has been particularly shown and described with reference to a preferred embodiment and several alternate embodiments, it will be understood by persons skilled in the relevant art that various changes in form and details can be made therein without departing from the spirit and scope of the invention.

What is claimed is:

1. A method for correcting errors resulting from differently illuminated eye fundus images, the method comprising the steps of:

obtaining at least two fundus images; selecting a first group of pixels from a first image;

selecting a second group of pixels from a second image, the second group of pixels associated with the first group of pixels;

determining an intensity level for at least one color channel for each pixel in each group of pixels in each image;

determining a mean intensity level and a variance for each group of pixels in each image; and altering the intensity level of pixels of the first group to approximate the intensity level of pixels in the second group by determining a new intensity level for both a first pixel of the first group and a corresponding second pixel of the second group, each intensity level being between the intensity level of the first pixel and the intensity level of the second pixel and altering the intensity level of the first and second pixels to be the new intensity level.

2. The method of claim 1 wherein the intensity level to be determined for each pixel is a function of grayscale values.

3. The method of claim 1 wherein the fundus images are obtained by an image capture device, and wherein the image capture device is moved between times when the first and second images are obtained.

4. The method of claim 3 wherein the step of selecting the first group of pixels further comprises:

selecting a plurality of pixels forming a line perpendicular to the direction of motion of the image capture device.

5. The method of claim 3 wherein the step of selecting the first group of pixels further comprises:

selecting a plurality of pixels forming a longitudinal line perpendicular to the direction of motion of the image capture device at a point where the longitudinal line intersects the direction of motion of the image capture device.

6. The method of claim 1 wherein the position of the fundus changes between the time the first and second images are obtained.

7. The method of claim 6 wherein the step of selecting the first group of pixels further comprises: selecting a plurality of pixels forming a line perpendicular to a direction of motion of the fundus.

8. The method of claim 6 wherein the step of selecting the first group of pixels further comprises:

selecting a plurality of pixels forming a longitudinal line perpendicular to a direction of motion of the image capture device at a point where the longitudinal line intersects the direction of motion of the fundus.

9. A system for correcting errors resulting from differently illuminated eye fundus images, comprising:

obtaining means for obtaining at least two fundus images;

a processing means coupled to the obtaining means, for processing image data;

a first selecting means coupled to the processing means, for selecting a first group of pixels of the first image;

a second selecting means, coupled to the processing means, for selecting a second group of pixels of the second image and associated with the first group of pixels;

a first determining means, coupled to the processing means, for determining an intensity level for at least one color channel for each pixel in each group of pixels in each image;

a second determining means, coupled to the processing means, for determining a mean intensity level and a variance for each group of pixels in each image; and altering means, coupled to the processing means, for altering the intensity level of pixels of the first group to approximate the intensity level of pixels in the second group by determining a new intensity level for both a first pixel of the first group and a corresponding second pixel of the second group, each intensity level being between the intensity level of the first pixel and the intensity level of the second pixel and altering the intensity level of the first and second pixels to be the new intensity level.

10. A computer-implemented method for correcting errors resulting from differently illuminated fundus images, the method comprising the steps of:

obtaining at least two fundus images;

selecting a first group of pixels from a first image;

selecting a second group of pixels from a second image, the second group of pixels associated with the first group of pixels;

determining an intensity level for at least one color channel for each pixel in each group of pixels in each image;

determining a mean intensity level and a variance for each group of pixels in each image; and altering the intensity level of pixels of the first group to approximate the intensity level of pixels in the second group by determining a new intensity level for both a first pixel of the first group and a corresponding second pixel of the second group, each intensity level being between the intensity level of the first pixel and the intensity level of the second pixel and altering the intensity level of the first and second pixels to be the new intensity level.

11. The method of claim 10, wherein the second group of pixels is selected according to a matching algorithm.

12. The method of claim 10, wherein the second group of pixels is selected such that the location of the first group in the first image is equivalent to the location of the second group in the second image.

13. A method for correcting illumination errors in multiple images of a fundus, the method comprising the steps of:

selecting a first group of pixels from a first image;

selecting a second group of pixels from the second image, the second group of pixels associated with the first group;

determining a first mean intensity value and a first variance for the pixels of the first group;

determining a second mean intensity value and a second variance for the pixels of the second group; and adjusting the intensity values of the pixels of the first group to have a new first mean intensity value, such that the new first mean intensity value is between the first mean intensity value and the second mean intensity value and adjusting the intensity value of the pixels of the second group to have a new second mean intensity value, such that the new second mean intensity value is equal to the new first mean intensity value.

14. The method of claim 13, wherein the step of adjusting the mean intensity values further comprises:

adjusting the intensity values of the pixels of the first group such that the first mean intensity value is equal to the second mean intensity value.

15. The method of claim 13, wherein the step of adjusting the mean intensity values further comprises:

adjusting the intensity values of the pixels of the second group such that the second mean intensity value is equal to the first mean intensity value.

* * * * *